United States Patent
Perry et al.

(10) Patent No.: US 10,470,458 B2
(45) Date of Patent: Nov. 12, 2019

(54) PLANT GROWTH REGULATION COMPOSITION

(75) Inventors: Richard Brian Perry, Bracknell (GB); Ian David Perry, legal representative, Bracknell (GB); Timothy Norman Perry, legal representative, Bracknell (GB); Ulrich Johannes Haas, Stein (CH); Philip Taylor, Bracknell (GB)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/007,365

(22) PCT Filed: Mar. 29, 2012

(86) PCT No.: PCT/EP2012/055605
§ 371 (c)(1),
(2), (4) Date: Sep. 25, 2013

(87) PCT Pub. No.: WO2012/130924
PCT Pub. Date: Oct. 4, 2012

(65) Prior Publication Data
US 2014/0378308 A1 Dec. 25, 2014

(30) Foreign Application Priority Data

Mar. 31, 2011 (GB) .................................. 1105526.6
Jul. 25, 2011 (GB) .................................. 1112815.4

(51) Int. Cl.
*A01N 25/30* (2006.01)
*A01N 37/42* (2006.01)

(52) U.S. Cl.
CPC ............. *A01N 25/30* (2013.01); *A01N 37/42* (2013.01)

(58) Field of Classification Search
CPC .... A01N 25/30; A01N 2300/00; A01N 33/12; A01N 37/42; A01N 43/40; A01N 43/54; A01N 43/653; A01N 47/02
USPC ................................................... 504/313, 358
See application file for complete search history.

(56) References Cited

U.S. PATENT DOCUMENTS

| 6,071,857 A * | 6/2000 | Vogt et al. ..................... 504/366 |
| 6,313,074 B1 * | 11/2001 | Suzuki et al. ................. 504/362 |
| 2011/0003875 A1 * | 1/2011 | Vermeer ................ A01N 25/04 514/409 |

FOREIGN PATENT DOCUMENTS

| DE | 19857963 | 6/2000 |
| EP | 1138202 | 10/2001 |
| WO | 9704653 | 2/1997 |

OTHER PUBLICATIONS

International Search Report/Written Opinion for International Patent Application No. PCT/EP2012/055605 dated Aug. 22, 2012.

* cited by examiner

*Primary Examiner* — Johann R Richter
*Assistant Examiner* — Courtney A Brown
(74) *Attorney, Agent, or Firm* — Baker & Hostetler, LLP; Toni-Junell Herbert

(57) ABSTRACT

The present invention relates to an improved plant growth regulation composition comprising a plant growth regulator and a surfactant. It also relates to a method for enhancing or regulating the growth of plants comprising applying said composition.

10 Claims, No Drawings

PLANT GROWTH REGULATION COMPOSITION

This application claims priority under 35 U.S.C. § 371 from PCT Application No. PCT/EP2012/055605, filed 29 Mar. 2012, which claims the benefit of European Patent Application 1105526.6, filed 31 Mar. 2011 and European Patent Application 1112815.4 filed 25 Jul. 2011, the disclosures of which are incorporated by reference herein.

The present invention relates to an improved plant growth regulation composition comprising a plant growth regulator and a surfactant. It also relates to a method for enhancing or regulating the growth of plants comprising applying said composition.

Plant growth regulators are often used to regulate the growth and development of crop plants. For example, plant growth regulators are used to slow the development of a crop (such as oil seed rape) so that it flowers at a desired time, reduce the height of a crop (such as in cereals) so that it is less susceptible to lodging, increase nitrogen efficiency, regulate flowering and fruit set of a crop (such as fruit trees), and slow turfgrass growth rate to reduce mowing frequency.

There are several different classes of plant growth regulator. Known classes include azoles (such as uniconazole, and paclobutrazol), cyclohexane carboxylates (such as trinexapac-ethyl, and prohexadione-calcium), pyrimidinyl carbinols (such as flurprimidol, and ancymidol), quarternary ammoniums (such as chlormequat-chloride, and mepiquat-chloride), and sulphonyl-amino phenyl-acetamides (such as mefluidide).

Plant growth regulators operate by various modes of action. For example, onium-type plant growth retardants such as chlormequat-chloride and mepiquat-chloride, that possess a positively charged ammonium, phosphonium or sulphonium group, function by blocking the synthesis of gibberellin early in the biosynthetic pathway. Growth retardants comprising a nitrogen-containing heterocycle, such as flurprimidol, paclobutrazol and uniconazole-P, act as inhibitors of monooxygenases that catalyse oxidative steps in gibberellin biosynthesis. Structural mimics of 2-oxoglutaric acid, such as the acylcyclohexanediones trinexapac-ethyl and prohexadione-calcium, interfere with the late steps of gibberellin biosynthesis. Other plant growth regulators, such as mefluidide, inhibit cell division and differentiation.

Plant growth regulators such as trinexapac-ethyl are commonly used on crops to reduce the risk of lodging through stem thickening and shortening, and improved rooting. It is well known in the art that treatment of crops with trinexapac-ethyl can increase yield both through reduction in lodging, and through improved rooting which makes the crop less susceptible to drought stress.

There is a need for improved plant growth regulating compositions that provide better growth regulating effects, both in terms of control of lodging and crop enhancement benefits.

It is known that adjuvants such as surfactants are often built into formulations, or added to tank mixtures before application, to improve uptake of the active ingredient into the plant. Surprisingly, it has been found that applying trinexapac-ethyl in combination with a specific surfactant results in better plant growth regulating effects than when applied alone, or with other surfactants. In particular, this allows excellent plant growth regulation and crop enhancement effects to be obtained at lower rates of plant growth regulator active ingredient.

According to the present invention, there is provided a composition comprising a plant growth regulator, a surfactant, and optionally an agriculturally acceptable carrier, wherein the surfactant is a branched non-ionic alcohol ethoxylate having an alkyl chain length of 8 carbon atoms, from 1 to 7 propylene oxide units, and from 4 to 9 ethylene oxide units.

In a further embodiment, there is provided a composition consisting essentially of a plant growth regulator, a surfactant, and optionally an agriculturally acceptable carrier, wherein the surfactant is a branched non-ionic alcohol ethoxylate having an alkyl chain length of 8 carbon atoms, from 1 to 7 propylene oxide units, and from 4 to 9 ethylene oxide units.

In a further embodiment, there is provided a composition consisting of a plant growth regulator, a surfactant, and optionally an agriculturally acceptable carrier, wherein the surfactant is a branched non-ionic alcohol ethoxylate having an alkyl chain length of 8 carbon atoms, from 1 to 7 propylene oxide units, and from 4 to 9 ethylene oxide units.

Suitably, the alkyl chain is ethyl-hexyl. The branching may be located at any position on the alkyl chain. Preferably, the alkyl chain is branched at the 2-position. More preferably the alkyl chain is 2-ethyl hexyl.

As is well known to those skilled in the art, the degree of ethoxylation represents a mean average, because the manufacturing process for such adjuvants is imprecise and results in products containing a distribution of molecules with different levels of ethoxylation.

In one embodiment, the surfactant comprises from 5 to 9 ethylene oxide units. In a further embodiment, the surfactant comprises from 7 to 8 ethylene oxide units. Preferably, the surfactant comprises an average of 8 ethylene oxide units.

In a further embodiment, the surfactant comprises from 4 to 7 propylene oxide units. In another embodiment, the surfactant comprises from 5 to 6 propylene oxide units. Preferably, the surfactant comprises an average of 6 propylene oxide units.

Suitably, the ratio of ethylene oxide to propylene oxide units is from 8:1 to 1:1. More suitably, the ratio of ethylene oxide to propylene oxide units is 3:1. More suitably still, the ratio of ethylene oxide to propylene oxide units is 4:3. Preferably, the ratio of ethylene oxide to propylene oxide units is from 1.1:1 to 1.6:1. In one embodiment, it is about 1.4:1.

Preferably the surfactant comprises (on average) 8 ethylene oxide and 6 propylene oxide units.

In one aspect of the present invention, the surfactant consists of 2-ethyl hexanol having an average of 6 PO units and an average of 8 EO units. In a further aspect, the surfactant consists of 2-ethyl hexanol having 2 PO units and 8 EO units.

In one embodiment, the surfactant is 2-ethyl hexanol PO-EO, which is available from Dow under the tradename Ecosurf® EH-6 (CAS 64366-70-7).

The composition of the present invention surprisingly provides better control of lodging at lower rates of active ingredient. Further, the ability to apply the composition at a lower AI rate without loss of plant growth regulation efficacy enables application at earlier plant growth stages—at a time when application of higher AI rates is typically phytotoxic to the plants. For example, on cereal crops the composition of the present invention may be applied at about growth stage 29-30, instead of growth stage 31-33. The ability to apply the composition at early growth stages maximises the crop enhancement benefits of the plant growth regulator compound itself, for example resulting in better root development, drought tolerance, and ultimately higher yield. The composition of the present invention may also give rise to a longer residual effect of the plant growth regulator, for example in terms of lodging control, crop enhancement benefits, or both.

Any plant growth regulator may be used in accordance with the present invention. A complete list of all commercially available plant growth regulators may be obtained from the Pesticide Manual (15$^{th}$ edition, published by the British Crop Protection Council). In one embodiment, the plant growth regulator is selected from the group consisting of trinexapac-ethyl, prohexadione-calcium, paclobutrazol, uniconazole, flurprimidol, mefluidide, mepiquat-chloride, chlormequat-chloride, and a mixture thereof.

Suitably, the plant growth regulator is a gibberellin biosynthesis inhibitor. Suitably, the plant growth regulator is a class A gibberellin biosynthesis inhibitor. Suitably, the plant growth regulator is a class B gibberellin biosynthesis inhibitor. In a preferred embodiment the plant growth regulator is trinexapac-ethyl, prohexadione-calcium or chlormequat-chloride. In one embodiment, the plant growth regulator is trinexapac-ethyl. In one embodiment, the plant growth regulator is prohexadione-calcium. In one embodiment, the plant growth regulator is chlormequat-chloride. In one embodiment, the plant growth regulator is paclobutrazol. In one embodiment, the plant growth regulator is flurprimidol.

In one embodiment, the composition of the present invention comprises at least 20% w/v surfactant. Suitably the composition of the present invention comprises at least 25% w/v surfactant. Suitably the composition of the present invention comprises at least 30% w/v surfactant. More suitably the composition of the present invention comprises at least 35% w/v surfactant. In a further embodiment, the composition of the present invention comprises at least 40% w/v surfactant. Preferably the composition of the present invention comprises about 40% w/v surfactant. Preferably the composition of the present invention comprises about 41% w/v surfactant. Preferably the composition of the present invention comprises about 42% w/v surfactant. Preferably the composition of the present invention comprises about 43% w/v surfactant. Preferably the composition of the present invention comprises about 44% w/v surfactant. Preferably the composition of the present invention comprises about 45% w/v surfactant. Preferably the composition of the present invention comprises about 46% w/v surfactant. Preferably the composition of the present invention comprises about 47% w/v surfactant. Preferably the composition of the present invention comprises about 48% w/v surfactant. Preferably the composition of the present invention comprises about 49% w/v surfactant. Preferably the composition of the present invention comprises about 50% w/v surfactant.

The plant growth regulator is present in the composition in an amount sufficient to regulate plant growth. In one embodiment, the composition of the present invention comprises between 5% and 95% active ingredient, preferably between 5% and 50%. In one embodiment, the composition comprises about 25% w/v active ingredient.

In the present invention, the mixture ratio of plant growth regulator to surfactant lies within the range from about 1:10 to about 10:1 by weight. Suitably, the mixture ratio of plant growth regulator to surfactant is from about 1:5 to about 5:1 by weight. More suitably, the mixture ratio of plant growth regulator to surfactant is from about 2:1 to about 1:2 by weight.

The composition of the present invention is typically diluted prior to use. In one embodiment of the present invention, there is provided a plant growth regulation spray solution comprising a composition as defined above, wherein the surfactant is present at between 0.1 and 0.5% w/v. Preferably, the surfactant is present in the spray solution at about 0.2% w/v.

The rate of application of the composition may vary within wide limits and depends upon the crop, the nature of the soil, the method of application, the prevailing climatic conditions, and other factors governed by the method of application and the time of application. The composition of the present invention is generally applied at a rate of 0.001 to 1 kg ai/ha, especially from 0.001 to 0.5 kg ai/ha. Suitably the composition is applied at a rate from about 50 to about 150 g ai/ha/ More suitably, the composition is applied at a rate of about 75 g ai/ha.

According to the present invention there is provided a method for enhancing the growth of plants comprising applying to a plant, plant part, plant propagation material, or plant growing locus a composition or plant growth regulation spray solution as defined above. In particular, the method results in improvements in plant yield, plant vigour, plant quality, and/or plant tolerance to stress factors. In one embodiment, the plants have improved tolerance to drought conditions.

The term 'crop enhancement' as used herein means an improvement in plant vigour, an improvement in plant quality, improved tolerance to stress factors, and/or improved input use efficiency.

According to the present invention, an 'improvement in plant vigour' means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant and/or less inputs needed (e.g. less fertiliser, water and/or labour needed). A plant with improved vigour may have an increase in any of the aforementioned traits or any combination or two or more of the aforementioned traits.

According to the present invention, an 'improvement in plant quality' means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g. seeds, fruits, leaves, vegetables (such improved quality may manifest as improved visual appearance of the harvested material, improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds) and/or improved seed quality (e.g. for use in following seasons). A plant with improved quality may have an increase in any of the aforementioned traits or any combination or two or more of the aforementioned traits.

According to the present invention, an 'improved tolerance to stress factors' means that certain traits are improved qualitatively or quantitatively when compared with the same trait in a control plant which has been grown under the same conditions in the absence of the method of the invention. Such traits include, but are not limited to, an increased tolerance and/or resistance to abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients.

According to the present invention, an 'improved input use efficiency' means that the plants are able to grow more effectively using given levels of inputs compared to the grown of control plants which are grown under the same conditions in the absence of the method of the invention. In particular, the inputs include, but are not limited to fertiliser (such as nitrogen, phosphorous, potassium, micronutrients), light and water. A plant with improved input use efficiency may have an improved use of any of the aforementioned inputs or any combination of two or more of the aforementioned inputs.

Other crop enhancements of the present invention include a decrease in plant height, or reduction in tillering, which are beneficial features in crops or conditions where it is desirable to have less biomass and fewer tillers.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

According to the present invention there is also provided a method for regulating the growth of plants comprising applying to a plant, plant part, plant propagation material, or plant growing locus a composition or plant growth regulation spray solution as defined above.

The composition of the present invention may be applied to any crop plants. Examples of dicotyledon crops include beet (such as sugar beet or fodder beet); fruits (such as pomes, stone fruits or soft fruits, for example apples, pears, plums, peaches, almonds, cherries, strawberries, raspberries or blackberries); leguminous plants (such as beans, lentils, peas or soybeans); oil plants (such as rape, mustard, poppy, olives, sunflowers, coconut, castor oil plants, cocoa beans or groundnuts); cucumber plants (such as marrows, cucumbers or melons); fibre plants (such as cotton, flax, hemp or jute); citrus fruit (such as oranges, lemons, grapefruit or mandarins); vegetables (such as spinach, lettuce, cabbages, carrots, tomatoes, potatoes, cucurbits or paprika); lauraceae (such as avocados, cinnamon or camphor); tobacco; nuts; coffee; tea; vines; hops; durian; bananas; natural rubber plants; and ornamentals (such as flowers, shrubs, broad-leaved trees or evergreens, for example conifers). This list does not represent any limitation. In one embodiment, the crop plants are oil plants. In particular, the crop plants are oil seed rape plants.

Examples of monocotyledon crops include cereals (wheat, millet, sorghum, rye, triticale, oats, barley, teff, spelt, buckwheat, fonio and quinoa), rice, maize (corn), turfgrass and sugar cane. Suitably the crop plants are monocotyledonous plants. More suitably, the crop plants are cereals, in particular wheat or barley. In one embodiment, the cereal crop is wheat. In a further embodiment, the cereal crop is barley. In a further embodiment, the crop plants are rice plants. In a further embodiment, the crop plants are sugar cane plants. In further embodiment, the crop plants are corn plants.

Suitably the crop plant is turfgrass. Cool season turfgrasses include, for example: Bluegrasses (*Poa* L.), such as Kentucky Bluegrass (*Poa pratensis* L.), Rough Bluegrass (*Poa trivialis* L.), Canada Bluegrass (*Poa compressa* L.) and Annual Bluegrass (*Poa annua* L.); Bentgrasses (*Agrostis* L.), such as Creeping Bentgrass (*Agrostis palustris* Huds.), Colonial Bentgrass (*Agrostis tenius* Sibth.), Velvet Bentgrass (*Agrostis canina* L.) and Redtop (*Agrostis alba* L.); Fescues (*Festuca* L.), such as Creeping Red Fescue (*Festuca rubra* L.), Chewings Fescue (*Festuca rubra* var. *commutata* Gaud.), Sheep Fescue (*Festuca ovina* L.), Hard Fescue (*Festuca longifolia*), Tall Fescue (*Festuca arundinacea* Schreb.), Meadow Fescue (*Festuca elatior* L.); Ryegrasses (*Lolium* L.), such as Perennial Ryegrass (*Lolium perenne* L.), Annual (Italian) Ryegrass (*Lolium multiflorum* Lam.); Wheatgrasses (*Agropyron* Gaertn.), such as Fairway Wheatgrass (*Agropyron cristatum* (L.) Gaertn.), Western Wheatgrass (*Agropyron smithii* Rydb.); Smooth Brome (*Bromus inermis* Leyss.); and Timothy (*Phleum* L.). Warm season turfgrasses include, for example Bermudagrasses (*Cynodon* L. C. Rich), Zoysiagrasses (*Zoysia* Willd.), St. Augustinegrass (*Stenotaphrum secundatum* (Walt.) Kuntze), Centipedegrass (*Eremochloa ophiuroides* (Munro.) Hack.), Carpetgrass (*Axonopus* Beauv.), Bahiagrass (*Paspalum notatum*

Flugge.), Kikuyugrass (*Pennisetum clandestinum* Hochst. ex Chiov.), Buffalograss (*Buchloe dactyloides* (Nutt.) Engelm.), Centipedegrass (*Eremochloa* spp) and Seashore paspalum (*Paspalum vaginatum* swartz).

Crops include those that have been rendered tolerant to herbicides like bromoxynil or classes of herbicides (such as HPPD inhibitors, ALS inhibitors (for example primisulfuron, prosulfuron and trifloxysulfuron), EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex IO and LibertyLink®. Crops also includes plants that have been transformed by the use of recombinant DNA techniques so that they are capable of synthesising one or more selectively acting toxins, such as are known, for example, from toxin-producing bacteria, especially those of the genus *Bacillus*. Crops also includes plants which have been transformed by the use of recombinant DNA techniques so that they are capable of synthesising antipathogenic substances having a selective action, such as, for example, the so-called "pathogenesis-related proteins". Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The composition of the present invention is typically formulated for use on plants, and further comprises formulation adjuvants, such as carriers, solvents and surface-active substances. The formulations can be in various physical forms, for example dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oil dispersions, suspoemulsions, capsule suspensions, emulsifiable granules, soluble liquids, water-soluble concentrates (with water or a water-miscible organic solvent as carrier), or impregnated polymer films. Such formulations can either be used directly or are diluted prior to use. Diluted formulations can be prepared, for example, with water, liquid fertilizers, micronutrients, biological organisms, oil or solvents. These formulations may contain as little as about 0.5% to as much as about 95% or more by weight of active ingredient. The optimum amount for any given compound will depend on formulation, application equipment and nature of the plants to be controlled.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles and are usually applied without dilution to the area in which suppression of vegetation is desired. Typical carriers for granular formulations include fertiliser, sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Particularly suitable is a fertiliser granule carrier. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins. The granular substrate material can be one of the typical carriers mentioned above and/or can be a fertiliser material e.g. urea/formaldehyde fertilisers, ammonium, liquid nitrogen, urea, potassium chloride, ammonium compounds, phosphorus compounds, sulphur, similar plant nutrients and micronutrients and mixtures or combinations thereof. The plant growth regulator and surfactant may be homogeneously distributed throughout the granule or may be spray impregnated or absorbed onto the granule substrate after the granules are formed.

Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule and may include solvent in addition to the active compound.

Other useful formulations for plant growth regulation applications include simple solutions of the active ingredients in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Many of the formulations described above include wetting, dispersing or emulsifying agents. Examples are alkyl and alkylaryl sulphonates and sulphates and their salts; polyhydric alcohols; polyethoxylated alcohols, esters and fatty amines. These agents, when used, normally comprise from 0.1% to 15% by weight of the formulation.

Suitable agricultural adjuvants and carriers, either formulated together and/or added separately, that are useful in formulating the compositions of the invention in the formulation types described above are well known to those skilled in the art. Suitable examples of the different classes are found in the non-limiting list below.

Liquid carriers that can be employed include water, toluene, xylene, petroleum naphtha, crop oils, AMS; acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaxeous earth, lime, calcium carbonate, bentonite clay, fuller's earth, fertiliser, cotton seed hulls, wheat flour, soybean flour, pumice, wood flour, walnut shell flour, lignin and the like.

In addition to the surfactant of the present invention, further surface-active agents may be advantageously employed in both said liquid and solid compositions, especially those designed to be diluted with carrier before application. The surface-active agents can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like. The compositions can also be formulated with liquid fertilizers or solid, particulate fertiliser carriers such as ammonium nitrate, urea and the like.

These formulations can be applied to plants pre- or post-emergence, by conventional methods, for example sprinkling, spreading or spraying (by hand, tractor, airplane and the like), drench or in-furrow application to soil, seed treatment, through addition to irrigation water and the like. Preferably the composition of the present invention is applied in the form of a spray application to the foliage plants after emergence.

The present invention may optionally include one or more additional pesticides such as insecticides, nematicides, fungicides or herbicides or additional plant growth regulators. A list of pesticides that may be used with the present invention is available in Pesticide Manual (15$^{th}$ edition, published by the British Crop Protection Council). For example, the composition of the present invention may comprise trinexapac-ethyl and paclobutrazol, trinexapac-ethyl and prohexadione-calcium, or trinexapac-ethyl and acibenzolar-5-methyl. Co-application of pesticides with the present invention has the added benefit of minimising farmer time spent applying products to crops, since only a single application may be required to both provide growth regulation and control pests.

The trinexapac-ethyl and further active ingredient may be applied either simultaneously or sequentially in any order. If administered sequentially, the components may be administered in any order in a suitable timescale, for example, with no longer than 1 month, no longer than 1 week, or no longer than 24 hours between the time of administering the first component and the time of administering the last component. Suitably, the components are administered within a timescale of a few hours, such as one hour. If the trinexapac-ethyl and further active ingredient are administered simultaneously, they may be administered separately or as a tank mix or as a pre-formulated mixture. In one embodiment the mixture or composition of the present invention may be applied to the crop plants as a seed treatment prior to planting.

EXAMPLES

Example 1

Summer barley, winter barley, summer wheat and winter wheat plants were grown in a glasshouse. Summer-barley was treated at beginning of stem elongation (GS32); winter barley, summer wheat and winter wheat plants were treated at the 3 leaf growth stage (GS13). Treatments were made as indicated in Table 1. Treatments were made by spraying with a boom sprayer and a spray volume of 200 l/ha. Treatments were made by tank mixing Moddus® with the relevant adjuvant. The adjuvants in treatments 2 and 3 were selected for their close structural similarity to that of treatment 1. The rate is expressed amount of trinexapac-ethyl (g ai/ha) and percentage of adjuvant in the spray solution.

TABLE 1

Treatment list

| Treatment | Trinexapac | Adjuvant | Rate (trinexapac g ai/ha + adjuvant %) |
|---|---|---|---|
| CHKa | Moddus ® (EC250) | None | 200 + 0 |
| CHKb | | | 100 + 0 |
| CHKc | | | 50 + 0 |
| 1a | Moddus ® (EC250) | Ecosurf EH6 (SL005) | 100 + 0.2 |
| 1b | | | 100 + 0.1 |
| 1c | | | 50 + 0.2 |
| 2a | Moddus ® (EC250) | Dowfax 20A64 (SL005) | 100 + 0.2 |
| 2b | | | 100 + 0.1 |
| 2c | | | 50 + 0. |
| 3a | Moddus ® (EC250) | Genapol X090 (SL005) | 100 + 0.2 |
| 3b | | | 100 + 0.1 |
| 3c | | | 50 + 0.2 |

Plant stand, including plant height and plant volume was assessed visually at 14, 21, 30 and 46 days after treatment, comparing treated plants against the untreated check. The results are shown in Table 2, expressed as a percentage of plant stand reduction compared to the relevant untreated control. Note that the 14 daa data is not presented because the plants were too young to demonstrate differences in plant height. Also, the 46 daa data is not presented because at this late growth stage the plants were beginning to ripen, and so the results did not give an accurate representation of the differences between treatments.

TABLE 2

Results - percentage plant stand reduction compared to control

| | 21 daa | | | | 30 daa | | | |
|---|---|---|---|---|---|---|---|---|
| Treatment | SB | WB | WW | SW | SB | WB | WW | SW |
| CHKa | 20 | 27.5 | 22.5 | 17.5 | 17.5 | 35 | 30 | 17.5 |
| CHKb | 7.5 | 2.5 | 10 | 5 | 7.5 | 5 | 15 | 10 |
| CHKc | 7.5 | 7.5 | 2.5 | 2.5 | 0 | 0 | 0 | 0 |
| 1a | 17.5* | 22.5* | 22.5* | 15* | 25* | 27.5* | 25* | 17.5* |
| 1b | 12.5* | 10* | 15* | 5* | 17.5* | 12.5* | 17.5* | 10* |
| 1c | 7.5 | 0 | 5* | 0 | 10* | 5* | 5* | 2.5* |
| 2a | 12.5^ | 7.5^ | 15^ | 10^ | 20^ | 5^ | 20^ | 12.5^ |
| 2b | 5^ | 10 | 15 | 5 | 10^ | 5^ | 15^ | 10 |
| 2c | 5^ | 10 | 5 | 0 | 5^ | 5 | 5 | 5 |
| 3a | 15^ | 7.5^ | 22.5 | 12.5^ | 20^ | 10^ | 27.5 | 17.5 |
| 3b | 7.5^ | 7.5^ | 17.5 | 7.5 | 7.5^ | 2.5^ | 17.5 | 15 |
| 3c | 5^ | 0 | 7.5 | 5 | 5^ | 0^ | 0^ | 10 |

SB = Summer barley (v. Passadena);
WB = Winter barley (v. Haaso);
WW = Winter wheat (v. Arina);
SW = summer wheat (v. Lona); daa = days after application
*= Better PGR effect than check at equivalent Moddus rates
^= Worse PGR effect than treatment 1 (less reduced plant stand)

The data shows that treatment 1 (Moddus+Ecosurf EH6) gave a much better plant growth regulation effect than the check (Moddus alone) treatments at equivalent rates of trinexapac-ethyl.

Further, the data shows that treatment 1 (Moddus+Ecosurf EH6) surprisingly resulted in a better plant growth regulation effect than treatments containing other adjuvants, (namely treatment 2 Moddus+Dowfax 20A64, and treatment 3 Moddus+Genapol X090), despite the close structural similarity and wetting properties of the adjuvants used in these treatments. Whilst there are a handful of data points for which treatment 1 gave a slightly worse plant growth regulation effect than treatments 2 or 3, the person skilled in the art will appreciate that this is probably due to natural variation that is inevitable in PGR biological trials—and that the overall data trend overwhelmingly supports the present invention.

Example 2

A field trial was setup in New Zealand. Treatments were applied to wheat, in the absence of lodging. The results in table 3 show that wheat treated with compositions of the present invention performed better than Moddus® applied at equivalent rates of trinexapac-ethyl, resulting in better reduction in height, and higher yield.

TABLE 3

Results - Height and yield of wheat

| Treatment | Rate of TXP (g ai/ha) | Height at 15DAA (cm) | Height at 35DAA (cm) | Yield (dt/ha) |
|---|---|---|---|---|
| Untreated | n/a | 71.5 | 70.6 | 104.5 |
| Moddus ® 250EC | 75 | 61.8 | 70.6 | 112.6 |
| Moddus ® 250EC | 100 | 58.5 | 68.8 | 118.2 |
| Composition of invention* | 75 | 58.4 | 68.6 | 118.3 |
| Composition of invention* | 100 | 57.3 | 65.8 | 127.7 |

*Contains 50% w/v Ecosurf EH6, and 25% w/v trinexapac-ethyl

Example 3

A field trial was setup in Brazil. Treatments were applied to various varieties of sugarcane 35 days before harvest, and the resulting amount of total recoverable sugars ('ATR') measured. The results (averages of replicates) in table 4 show that the sugarcane treated with a composition of the present invention results in higher a level of ATR than Moddus® at lower rates to trinexapac-ethyl.

TABLE 4

Results - Total recoverable sugars in sugarcane

| | Rate of | ATR (kg/ton of sugarcane) | |
|---|---|---|---|
| Treatment | TXP (g ai/ha) | Variety SP816250 | Varieties RB855453; SP791011; SP813250 |
| Untreated | n/a | 136.52 | 128.66 |
| Moddus ® 250EC | 150 | 135.77 | 133.25 |
| Moddus ® 250EC | 200 | 137.79 | 134.57 |
| Moddus ® 250EC | 250 | 138.12 | 135.56 |
| Composition of invention* | 113 | 144.5 | 133.49 |
| Composition of invention* | 150 | 144.68 | 135.74 |
| Composition of invention* | 188 | 149.58 | 139.76 |

*Contains 50% w/v Ecosurf EH6, and 25% w/v trinexapac-ethyl

The invention claimed is:
1. A composition comprising a plant growth regulator, a surfactant, and optionally an agriculturally acceptable carrier, wherein the surfactant is a branched non-ionic alcohol ethoxylate having an alkyl chain length of 8 carbon atoms, an average of from 5 to 6 propylene oxide units, and an average of from 7 to 8 ethylene oxide units, as represented by the general formula:

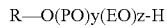

R—O(PO)y(EO)z-H wherein R is an alkyl with 8 carbon atoms, y is 5-6 and z is 7-8, and wherein the plant growth regulator is trinexapac-ethyl; and wherein the composition provides and improvement in plant growth reduction when compared to a composition having an equivalent rate of trinexapac-ethyl but without the surfactant.

2. A composition according to claim 1, wherein the alkyl chain is ethyl-hexyl.

3. A composition according to claim 1, wherein the surfactant is 2-ethyl hexanol 6PO-8EO.

4. A composition according to claim 1 comprising at least 20% w/v surfactant.

5. A plant growth regulation spray solution comprising a composition as defined in claim 1, wherein the surfactant is present at between 0.1 and 0.5% w/v.

6. A plant growth regulation spray solution according to claim 5, wherein the surfactant is present at about 0.2% w/v.

7. A method for enhancing the growth of plants comprising applying to a plant, plant part, plant propagation material, or plant growing locus a composition as defined in any one of claim 1.

8. A method according to claim 7, wherein enhancing includes at least one of improving plant yield, plant vigour, plant quality, plant tolerance to stress factors, and input use efficiency.

9. A method according to claim 8, wherein the plant has improved tolerance to drought conditions.

10. A method for regulating the growth of plants comprising applying to a plant, plant part, plant propagation material, or plant growing locus a composition as defined in claim 1.

* * * * *